Figure 1:
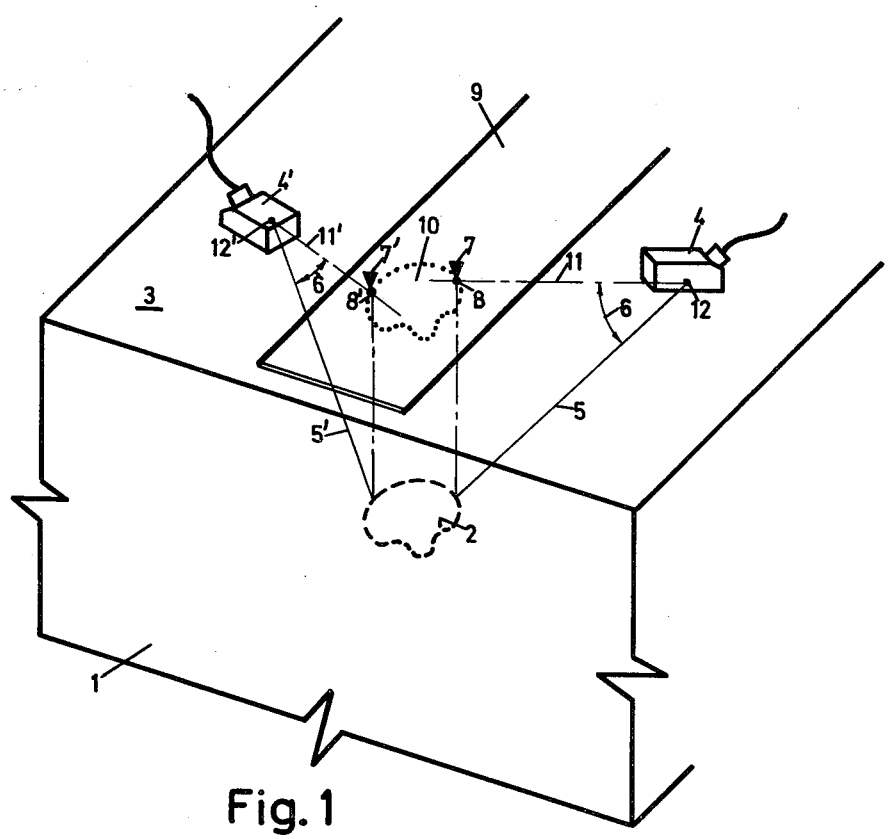

United States Patent [19]
Lund et al.

[11] 3,939,697
[45] Feb. 24, 1976

[54] METHOD AND APPARATUS FOR ULTRASONIC EXAMINATION

[75] Inventors: Svend Aage Lund, Birkerod; Palle Rasmus Jensen, Vanlose, both of Denmark

[73] Assignee: Akademiet for de Tekniske Videnskaber, Svejsecentralen, Glostrup, Denmark

[22] Filed: Mar. 8, 1973

[21] Appl. No.: 339,215

[30] Foreign Application Priority Data
Aug. 28, 1972 Denmark............................ 4256/72

[52] U.S. Cl.............................................. 73/67.8 S
[51] Int. Cl.²......................................... G01N 29/04
[58] Field of Search............ 73/67.7, 67.8 R, 67.8 S, 73/67.9

[56] References Cited
UNITED STATES PATENTS

| | | | |
|---|---|---|---|
| 2,836,059 | 5/1958 | Beaujard et al. .................. | 73/67.8 S |
| 3,518,697 | 6/1970 | Martens........................ | 73/67.8 S X |
| 3,555,888 | 1/1971 | Brown .............................. | 73/67.8 S |
| 3,688,564 | 9/1972 | McDicken ........................ | 73/67.8 S |

FOREIGN PATENTS OR APPLICATIONS

| | | | |
|---|---|---|---|
| 696,920 | 9/1953 | United Kingdom.................. | 73/67.7 |
| 1,509,554 | 12/1967 | France.............................. | 73/67.8 S |

OTHER PUBLICATIONS
D. Sproule, An Ultrasonic Imaging System for Flaw Detection Ultrasonics for Industry, 1969 conference papers, London, England, 7–8 Oct. 1969, S01200014.

*Primary Examiner*—Richard C. Queisser
*Assistant Examiner*—John P. Beauchamp
*Attorney, Agent, or Firm*—Schuyler, Birch, Swindler, McKie & Beckett

[57] ABSTRACT

Method and apparatus are disclosed in which it is possible by means of ultrasonic examination according to the pulse echo method to obtain an indication, or a recording of images, of internal inhomogeneities in otherwise homogeneous bodies, corresponding substantially to the images obtained by producing a normal radiographic film of the body. To obtain this an ultrasonic angle probe is moved across the surface of the body and the echo signals are used to produce punctiform markings on a recording surface in such a way that (a) the markings are effected along a moving axis of indication, (b) the displacement of a reference point on the axis of indication follows the displacement of the sound emission point of the probe, (c) the direction of the axis of indication follows the direction of the projection of the sound path on the surface of the body, and (d) the distance from the reference point to each marking is proportional to the echo time of the corresponding ultrasonic pulse. Various methods of recording, including remote recording, are described.

31 Claims, 13 Drawing Figures

METHOD AND APPARATUS FOR ULTRASONIC EXAMINATION

The present invention relates to a method of indicating, or of recording images, of internal inhomogeneities in otherwise homogeneous bodies that have a substantially plane or slightly curved surface, by ultrasonic examination according to the pulse echo method, use being made of at least one angle probe which is guided across the surface of the body and scans its interior by emitting and receiving short-durations ultrasonic pulses in directions that form a predetermined angle differing from 90° with the surface of the body.

The ultrasonic examination process according to the pulse echo method for the determination of internal inhomogeneities in otherwise homogeneous bodies is widely used, on the one hand, within the technique for determining internal flaws or voids in e.g. rolled, cast or welded bodies and, on the other hand, within the field of medical or veterinary diagnostic for determining the shape and location of internal organs or interfaces in living organisms.

In those cases where a part of the surface of the body is inaccessible or irregular to such a degree, as, by way of example, the uneven top bead of a weld, that it is impossible or less expedient to place the probe on the surface directly above the area of which the examination is required, an angle probe is employed that is placed on the nearest accessible and plane portion of the surface, for instance, next to a weld, whereupon the sound pulses are sent obliquely into the area of the body which it is desired to examine and in directions that form a predetermined angle differing from 90° with the surface of the body.

It has turned out to be a big problem with this method to achieve a certain and expeditious registration of the exact size and location of the internal inhomogeneities discovered since, for each individual location of the probe, an accurate measuring and registering operation of the location of the sound entry point on the surface of the body and of the angle in which the probe is placed on the surface of the body has to be effected. Simultaneously herewith, by means of the ultrasonic apparatus, a reading or registration of the time interval that has elapsed from the emission to the reception of the reflected ultrasonic pulses has to be undertaken, which time interval is proportional to the total distance the ultrasonic pulse has travelled inside the body including possible reflections from other points of the surface of the body. Finally, from the values thus measured, a geometric computation or construction of the coordinates of the reflection point discovered in the interior of the body has to be carried out, subsequent to which it is possible to register them or to mark them on a drawing of the tested body.

This whole procedure has thereafter to be repeated a great many times with the probe placed in a number of different positions and at different angles in order to locate and chart merely one single internal flaw or so as to describe and identify one single internal inhomogeneity in the body.

In practice, when systematically examining larger bodies, long welds and the like, this method becomes exceedingly time-consuming and is, furthermore, subject to significant error factors since the operator, during the entire course of the testing operation, has to keep track of and operate with a great number of measurings and geometrical computations. Consequently, the accuracy of the overall testing result very largely depends on the personal efficiency, patience and reliability of the individual operator.

In order to obviate these disadvantages, great efforts have been made to develop better methods. Attempts have been made, on the one hand, to mechanize the movement of the probe across the surface of the body as well as to reduce the time taken in testing by the concurrent employment of a large number of ultrasonic probes and, on the other hand, endeavours have been directed to automating the registration and the computational processing of the many measuring values involved.

A synopsis of the methods evolved so far is provided in the journal "Materialpruefung" No. 10, 1970, pages 329–336. It appears herefrom that none of the prior art methods have succeeded in leading to a satisfactory solution of the task involved. On the other hand, they require the employment of extremely complicated mechanical and electronic apparatus systems and, on the other hand, the testing accuracy is inadequate to provide the requisite power of resolution in respect of the details of the flaws discovered, moreover, they only furnish a registration in the form of an intermediate product which subsequently has to undergo an extensive manual or computational processing before a collective charting and identification of all the flaws discovered in an examined body can be available.

A typical example of the prior art is the method described in U.S. Pat. No. 3,585,851, in which the measuring values registered in the testing of a weld appear as a number of curves on a measuring strip from a multi-channel recorder. A collective charting and identification of the flaws discovered can only be effected by means of an extensive manual or computational processing and by an evaluation of the shape and course of the curves registered.

Another typical example of the prior art is the sectional view method or the so-called "B-scan," in the way this has been described in e.g. British Patent Specification No. 863,874 and U.S. Pat. No. 3,178,933. In these methods, the ultrasonic probe is conducted in a reciprocal movement along a straight line on the surface of the body whereby the emitted ultrasonic pulses scan a sectional plane of the body at right angles to its surface. By means of a special mechanical and electronic connection to an ultrasonic apparatus incorporating a cathode ray screen having a long afterglow period or an electronically controlled "storage screen," a stationary, persistent image is produced that shows the location of the reflection points discovered in the sectional plane in question through the body.

This method, which represents a significant advance in the desired direction, has gained wide application in technical and medical practice, but it still is subject to important shortcomings when larger bodies or long welds are to be examined in industrial practice. The image produced represents each time only a single section of the examined body and thus still constitutes only an intermediate product in the examination of the body. A collective charting of all the flaws discovered in a larger body calls for producing and registering or, possibly, photographing a large number of sectional views at different distances and mutual angles, following which these sectional views can only later, by means of an extensive manual or computational processing operation, be compounded into the desired, collective geometrical reproduction of the inhomogeneities or flaws discovered, corresponding to the collective image obtained by producing a normal radiographic film of the body.

It is the object of the present invention to eliminate all the above shortcomings of the prior art by providing a method of indicating or of directly recording two-dimensional projection images of internal inhomogeneities in a homogeneous body to be examined in such a way that, by means of ultrasonic examination in a single operation, an accurate geometric reproduction of all the internal inhomogeneities in the body is produced in a rapid and reliable manner, which reproduction, in its nature, fully corresponds to the image provided by producing a radiographic film of the body.

In addition, it is the object of the invention to provide a method of ultrasonic examination that is equally well suited for being carried out by manual or automatic guiding of the ultrasonic probe across the surface of the body and whereby a substantial simplification of the requisite mechanical and electronic apparatus systems is achieved, a complete elimination of the purely human error factors on the part of the operator himself, an increase in the power of resolution in respect to details in the flaws discovered, as well as the possibility of producing a permanent, visual documentation of the result of the examination which is obtained in a by far faster and cheaper manner than the radiographic examination method which is otherwise often preferred just for this very reason.

This is achieved according to the invention by employing indicating means which, by being activated when reflected sound pulses are received, produce punctiform markings on a substantially plane recording surface, in that the markings on the recording surface are effected along a moving axis of indication which is guided in such a way in the plane of the recording surface that the displacement of a reference point on the axis of indication in relation to the recording surface follows the two-dimensional displacement of the sound emission point of the probe in relation to the surface of the body on a predetermined scale, and that the direction of the indication axis in relation to the recording surface follows the direction of the projection of the sound path on the surface of the body, each marking being effected at a distance from the reference point that is proportional to the time interval that has elapsed from the emission to the reception of a sound pulse.

It is achieved hereby that the probe, as the examination operation gradually proceeds, can be guided entirely freely across the surface of the body at different distances from and at different angles in relation to the present internal inhomogeneities continually emitting and receiving ultrasonic pulses, while nevertheless a geometrically correct marking of each and every one of the reflected sound pulses takes place in accordance with the location of the point of reflection in the interior of the body in such a way that the markings may successively be summed up into a coherent image of the projection on the surface of the body of all the internal inhomogeneities which are encountered by the sound beam and reflect this back to the sound head.

It will be possible to effect the practical execution of the fundamental method provided by the invention by employing many different facilities normal to the prior art and in many different ways which will now be immediately obvious to any expert who is familiar with the known technique of ultrasonic examination and of automatic recording of measuring results in general.

A first embodiment of the method according to the invention is characterized in that a recording material is placed immediately above and parallel to the surface of the examined body and rigidly connected thereto, and in that indicating means are employed that are rigidly connected to the probe in such a way that the axis of indication is coincident with the projection of the sound path on the recording material, and that the reference point is coincident with the sound emission point. In addition to an extraordinarily simple recording operation, the advantage is obtained hereby that the recording takes place immediately above the point where the inhomogeneities are located.

A particularly simple embodiment of the method according to the invention is characterized in that the marking operation is effected by employing at least one line of indicating units that are mounted at fixed intervals along the axis of indication and in rigid connection with the probe, each individual indicating unit, in a manner known per se, being further connected to the receiver part of the ultrasonic apparatus via control circuits in such a way that the individual indicating unit is activated when and only when a signal is generated from a reflected sound pulse, the total time taken by which for forward and return travel in the body is proportional in a specific, predetermined relationship to the distance from the sound emission point of the probe to the indicating unit in question.

By means of this embodiment, in which the indicating units are mounted in line along, for instance, a ruler that is directly connected to a conventional probe, a particularly simple testing method is achieved, in particular for manual ultrasonic examination. The operator now merely needs to concentrate his attention on carrying out a thorough scanning of the entire testing area and he no longer has to make any readings or measurings and does not have to undertake any form of computations or take notes during the course of the examination operation proper. He is able to follow directly in front of the probe, the successive formation of the projection image of the internal reflection points and can, fully freely, continue the scanning of a specific part area of the body until a satisfactory image of the discovered flaws or the like has been recorded, subsequent to which he can continue on to the next part area and thus on further until he has produced a satisfactory collective projection image of the entire examined body.

A first expedient recording method of the kind described is characterized in that conventional styluses are used as indicating units which, by being activated electrically, produce a punctiform marking on the associated recording material.

Hereby, in many instances, by employing ordinary writing paper or electrosensitive paper which is taken from a roll and stretched across the body, for example, in the form of a narrow strip across the full length of a rather long weld, a particularly inexpensive method is achieved.

Another expedient embodiment of the method according to the invention is characterized in that at least one line of substantially punctiform light diodes are employed as indicating units which are mounted at fixed intervals and in rigid connection with the probe along a straight line which substantially coincides with the projection of the sound path on the surface of the body, each individual light diode being further connected, in a manner known per se, to the receiver part of the ultrasonic apparatus via control circuits in such a way that the individual light diode is activated to appear as a luminous point when and only when a signal is generated from a reflected sound pulse, the total time taken by which for forward and return travel in the body is proportional in a specific, predetermined relationship to the distance from the sound emission point of the probe to the light diode in question.

Hereby the advantage can be obtained that the operator, thanks to the luminous points, in an expeditious and clear manner, has pointed out to him that internal reflection points do exist inside the body, which, perhaps, call for a more thorough local scanning of the area thus indicated. In certain instances, in the case of simpler or more makeshift, orienting testing operations, it might even be sufficient for the luminous points to be registered by the eyes of the operator without any other form of registration of a more permanent nature being effected. In such cases, the method according to the invention can serve as a particularly valuable, supplementary aid for the operator when carrying out a normal, manual ultrasonic examination.

According to the invention the punctiform markings caused by said light diodes may be produced on a photosensitive recording material placed immediately above and parallel to the surfaces of the examined body and rigidly connected thereto.

Hereby is in many cases obtained a particularly high degree of accuracy in the reproduction of the projection images, which can be recorded on ordinary photographic paper or on conventional photographic film.

However, the punctiform markings caused by said light diodes may also be produced on a photosensitive recording material placed above and parallel to the surface of the examined body in a stationary photographic camera whose shutter is open.

A second expedient recording method of the kind described where styluses are used is characterized in that above each stylus and on the side facing away from the surface of the body, in addition, a substantially punctiform light diode is additionally mounted that is activated simultaneously with the stylus in question and thereby provides a visual indicating every time a marking is produced on the recording material.

An inexpensive, permanent form of recording is achieved hereby on conventional registration paper while, at the same time, the operator obtains valuable information to the effect that a marking takes place at the moment in question.

A third expedient method of recording of the kind described in which, in connection with the ultrasonic apparatus, a cathode ray tube is employed in a conventional manner, on the fluorescent screen of which video signals from the reflected sound pulses produce luminous points or dashes along a time deflection axis and at distances that are proportional to the total amount of time taken in travelling forward and back by the sound pulses in the body, is characeristed in that flexible light conductors with substantially punctiform cross-section are employed as indicating units whose first end is mounted on the axis of indication and facing a photosensitive recording material and whose second end is mounted immediately in front of and facing the screen of the cathode ray tube at a distance along the time deflection axis of the screen that is proportional to the distance from the sound emission point of the probe to the first end of the light conductor, whereby a light marking on the screen opposite the second end of the light conductor is transmitted via the light conductor and thereby produced a corresponding, punctiform marking on the photosensitive recording material at the surface of the body.

In every ultrasonic examination according to the plus echo method it will be necessary anyhow to employ a conventional image of the ultrasonic pulses of a cathode ray screen in the so-called "A-scan" for setting and adjusting the sound pulses as well as for a continuous surveillance of the satisfactory functioning of the apparatus during the entire examination. By means of the method indicated here, an expedient, direct utilization of the luminous points and dashes produced anyhow is achieved for recording the projection images, simultaneously with a significant simplication of the equipment used being attained, in that both the many indicating means with associated, individual conductors, as well as all the associated electronic control and checking equipment can now be dispensed with altogether and be simply replaced by a single bundle of conventional, flexible light conductors.

An expedient embodiment of the method according to the invention, in which the recording material is placed immediately above and parallel to the surface of the examined body and rigidly connected with it, is characterized in that the marking is effected by employing at least one indicating unit which is displaceably mounted in a holder that is in rigid connection with the probe, which indicating unit is made to execute a continually repeated movement along the axis of indication, in addition to which the indicating unit, in a manner known per se, via a position transducer and control circuits, is electrically connected to the receiver part of the ultrasonic apparatus in such a way that the indicating unit is activated when and only when a signal is generated from a reflected sound pulse, the total time taken by which in forward and return travel in the body is proportional in a specific, predetermined relationship to the distance from the sound emission point of the probe to the point where the indicating unit happens to be when the sound pulse is received.

It is possible hereby to achieve a simplification of the method in relation to the embodiments described in the foregoing in that the more complicated function, the wiring to and control of a large number of indicating units can be avoided when these units are replaced by a single, displaceable indicating unit whose actual position, in a known and simple manner, can be ascertained via a conventional position transducer and associated control circuits.

A first expedient registration method of the kind described is characterized in that at least one indicating unit is employed which is made to perform a continually repeated reciprocating movement along the axis of indication.

A second expedient registration method of the kind described is characterized in that at least one indicating unit is employed that is mounted in rigid connection with an endless belt running around two rollers, the shafts of which are rigidly connected to the probe and are mounted parallel to the recording material and perpendicular to the axis of indication, whereby the indicating unit is made to carry out a continually repeated movement in the same direction along the axis of indication.

A third expedient registration method of the kind described is characterized in that a facsimile registration device is employed as indicating unit, which device consists of a cylinder provided with a helical projection and rotating around a shaft that is rigidly connected to the probe and is mounted parallel to the axis of indication, whereby the point of contact between the helical projection and the recording material is made to execute a continually repeated movement in the same direction along the axis of indication.

A further expedient embodiment of the method according to the invention is characterized in that the recording material is separated from the tested body and mounted in a first holding device which, via a first mechanical or electrical connection, is connected to the body, in addition to which indication units are mounted in a conventional marking position in relation to the recording material along the axis of indication and in another holding device which, via a second mechanical or electrical connection, is connected to the probe.

By means of this embodiment, in which the recording material and the indicating units are separated from the examined body, firstly, a simplification of the examination procedure itself is achieved, which may now be carried out with a quite conventional ultrasonic probe which only has to be mounted in a holding device for recording the two-dimensional displacement of the probe across the surface of the body. Secondly, it is possible to keep the recording material and the relatively vulnerable indicating units protected against shocks, humidity and fouling from the examined body itself and, finally and thirdly, full freedom of choice according to the prevailing conditions is achieved in regard to letting the body or the sound head, or both, move during the course of the examination, since, in all instances, the relative movement between the body and the probe is correctly transmitted and reproduced.

The mechanical or electrical connecting systems required for this purpose may be constructed and designed in many different ways according to the prior art. Examples of the connecting systems of this category which may be employed are described, inter alia, in the patent specifications quoted in the foregoing, that is to say the specifications of British Pat. No. 863,874 and U.S. Pat. Nos. 3,178,933 and 3,585,851.

A further development of this embodiment of the method according to the invention, in which both the recording material and the indicating means are separated from the examined body, is characterized in that a fluorescent screen of a cathode ray tube is employed as recording material and in that a controlled electron beam is used as indicating means, which beam produces luminous points on the screen by means of intensity modulation, in addition to which the two-dimensional displacement of the probe across the surface of the body, in a manner known per se, via a mechanical or electrical connection and position transducers as well as electronic control circuits, is converted into such control voltages for the electron beam of the cathode ray tube that the beam, at all times and on a predetermined scale, follows a rectilinear track on the screen which consittutes the axis of indication, in addition to which the video signal produced in the ultrasonic apparatus by the reception of a reflected sound pulse and the associated deflection voltage, in a manner likewise known per se, via electronic control circuits and intensity modulation circuits, is used to produce a luminous point on the axis of indication when the probe receives a reflected sound pulse, and at a distance from the reference point of the axis of indication which, on the same predetermined scale, is proportional to the time interval that has elapsed from the emission to the reception of the sound pulse.

It is hereby achieved that the entire recording operation can be carried out by purely electronic means without any mechanical indicating means and associated guiding means being employed. The operator is able to follow the successive formation of the projection image on the screen of the cathode ray tube and, with full freedom of choice, he is in a position to continue the scanning of a specific part area of the body until a satisfactory image of the discovered flaws and the like has been formed. The finished projection image can subsequently be studied at once and photographed for permanent documentation.

A particularly expedient registration method of the kind described is characterized in that, for the determination of the actual position and direction of the ultrasonic probe in relation to the surface of the body, two rectilinear microphones are employed that are mounted at right angles to each other immediately above the surface of the body and parallel to it, in addition to which, in rigid connection with the ultrasonic probe, two substantially punctiform sound sources are mounted for the emission of spherical sound waves, one of them immediately above the sound emission point of the ultrasonic probe and the other at a distance herefrom immediately above the projection of the sound path on the surface of the body, following which the two punctiform sound sources, alternately and at brief time intervals, are made to emit short-duration spherical sound waves which, a little later, are received and registered by the two linear microphones, in addition to which the four time intervals from the emission to the reception of the two spherical sound waves, which time intervals are proportional to the perpendicular distances from the sound sources to the linear microphones, in a manner known per se, via coordinate registration circuits and electronic control circuits, are converted into control voltages for the corresponding, correct location and direction of the track of the electron beam on the screen of the cathode ray tube.

By this special application of the technique that is known per se, for acoustic position determination and coordinate reading, it is achieved that the untrasonic examination proper can be carried out quite unimpededly in a completely conventional manner and entirely without any complicated, bulky and vulnerable mechanical guiding means and associated position transducers. The method provided according to the imvention hereby becomes particularly convenient to carry out for the operator while, at the same time, it is possible to keep the entire, more vulnerable part of the electronic control and recording system completely separated from and protected against the influences of the examined body itself.

The various systems described for carrying out the method of the ultrasonic examination and the electronic transmission and recording of the measuring results from part of the generally known prior art and must only be regarded as illustrative examples of the many corresponding methods and systems which it will be obvious to a person skilled in the art to employ in connection with carrying out the fundamental method of directly recording two-dimensional projection images provided by the present invention. Typical examples of employing the prior art registration technique by means of cathode ray tubes are thus described in the specifications of British Pat. No. 863,874 and U.S. Pat. No. 3,178,933 quoted above.

It would, for example, likewise be obvious to employ the prior art for temporary or permanent electric, electronic or magnetic storage of the recorded measuring data and registration pulses etc., with a view to a desired reading or recreating at a later time of the projection images produced by means of the method.

The invention also relates to an apparatus to be employed in carrying out the method according to the invention, comprising an ultrasonic apparatus provided with one or several angle probes as well as indicating means which, by being activated when reflected sound pulses are received, produce punctiform markings on a substantially plane recording surface, which apparatus is characterized in that the indicating means are adapted to produce markings on the recording surface along a moving axis of indication and to guide this axis in such a way in the plane of the recording surface that the displacement of a reference point on the axis of indication in relation to the recording surface follows the two-dimensional displacement of the sound emission point of the probe in relation to the surface of the body on a predetermined scale, and that the direction of the axis of indication in relation to the recording surface follows the direction of the projection of the sound path on the surface of the body, as well as to produce markings at a distance from the reference point which is proportional to the time interval that has elapsed from the emission to the reception of a sound pulse.

An embodiment of this apparatus to be employed in connection with a recording material placed immediately above and parallel to the surface of the examined body and in rigid connection thereto is characterized in that the indicating means are rigidly connected to the probe in such a way that the axis of indication is coincident with the projection of the sound path on the recording material and that the reference point coincides with the point of sound emission. In this case it is ensured in a particularly simple manner that the axis of indication and its reference point follow the projection of the sound path and the sound emission point in the prescribed manner.

A particularly simple embodiment of the last-mentioned apparatus is characterized in that a holder provided with at least one line of indicating units is mounted in rigid connection to the probe, which indication units are mounted at fixed intervals along a straight line that is coincident with the projection of the sound path on the plane of the recording material, and in that each individual indicating unit, in a manner known per se, via control circuits, is so connected to the receiver part of the ultrasonic apparatus that the individual indicating unit is activated and produces a punctiform marking on the recording material when and only when a signal is generated from a reflected sound pulse, the total time taken by which for forward and return travel in the body is proportional in a specific, predetermined relation to the distance from the sound emission point of the probe to the indicating unit in question.

In an expedient embodiment of the apparatus, the indicating units are styluses which by being electrically activated, produce a punctiform marking on the associated recording material.

Another expedient embodiment of the apparatus according to the invention is characterized in that a holder provided with at least one line of light diodes is mounted in rigid connection to the probe, which light diodes are mounted at fixed intervals along a straight line which substantially coincides with the projection of the sound path on the surface of the body, and in that each individual light diode, in a manner known per se, via control circuits is connected to the receiver part of the ultrasonic apparatus in such a way that the individual light diode is activated to appear as a luminous point when and only when a signal is generated from a reflected sound pulse, the total time taken by which for forward and return travel in the body is proportional in a specific, predetermined relationship to the distance from the sound emission point of the probe to the light diode in question.

In this embodiment the light diodes can, according to the invention, be arranged in such a way that they can produce punctiform markings on an associated photosensitive recording material placed immediately above and parallel to the surface of the examined body and rigidly connected thereto.

However, the light diodes may also be arranged in such a way that they can produce punctiform markings on a photosensitive recording material placed above and parallel to the surface of the examined body in a stationary photographic camera whose shutter is open.

In a further expedient embodiment of the apparatus where styluses are used there is, above each stylus and on the side of the holder facing away from the surface of the examined body, additionally mounted a substantially punctiform light diode which is activated simultaneously with the stylus in question and which thereby provides a visual indication every time a marking is produced on the recording material.

With the aid of the embodiments described it is achieved that the entire recording system for the production of projection images consists of two standard elements only, a simple and sturdy holder provided with fixed indicating units devoid of displaceable components and directly mountable on any conventional angle probe, and a supplementary unit with electronic control circuits that can be directly connected to a conventional ultrasonic apparatus.

In yet another expedient embodiment of the apparatus, in which the ultrasonic apparatus is equipped with a conventional cathode ray tube on whose screen video signals from the reflected sound pulses produce luminous dots or dashes along a time deflection axis at distances which are proportional to the total time taken by the sound pulses for forward and return travel in the body, the indicating means comprise flexible light conductors having a substantially punctiform cross-section, the first end of which is mounted in rigid connection with the probe and facing the recording material, and the second end of which, in a holder, is mounted immediately in front of and facing the screen of the cathode ray tube at a distance along the time deflection axis of the screen which is proportional to the distance from the sound emission point of the probe to the first end of the light conductor.

By means of this embodiment the additional simplification is achieved that the electronic control circuits can be dispensed with altogether so that the recording system comes to consist of nothing but a simple and sturdy holder with flexible light conductors, the opposite end of which, with the aid of a corresponding simple and sturdy holder, merely has to be placed in front of the screen of a conventional ultrasonic apparatus.

In a further expedient embodiment, the apparatus is characterized in that, rigidly connected to the angle probe, a holder is mounted in which at least one indicating unit is mounted that is displaceable in such a way in relation to the holder that it can be moved along a straight line which is parallel to the projection of the sound path on the recording material, as well as in that the indicating unit, in a manner known per se, via a position transducer and control circuits, is connected to the receiver part of the ultrasonic apparatus in such a way that the indicating unit is activated and produces a punctiform marking on the recording material when and only when a signal is generated from a reflected sound pulse, the total time taken by which for forward and return travel in the body is proportional in a predetermined relationship to the distance from the sound emission point of the probe to the point where the indicating unit happens to be when the sound pulse is received.

In a special embodiment of this registration system, at least one indicating unit is mounted in rigid connection with an endless belt running around two rollers, the shafts of which are rigidly connected to the probe and are mounted parallel to the recording material.

In another special embodiment of this recording system, a conventional facsimile registration device is employed having a cylinder provided with a helical projection and rotatable around a shaft that is rigidly connected to the probe and is mounted parallel to the recording material.

With the aid of the thus described embodiments with displaceably mounted indicating units it is possible to achieve a simplification of the recording system as compared to the previously described system which require a complicated wiring system for and the control of a large number of indicating units.

A further expedient embodiment of the apparatus according to the invention is characterized in that a substantially plane recording material is placed in a first holding device which, via a first mechanical or electrical connection, is connected to the examined body in such a way that the holder follows the two-dimensional displacement of said body in the plane of the surface on a predetermined scale, and in that at least one indicating unit is mounted in a conventional marking position in relation to the recording material and secured in a second holder which, via a second mechanical or electrical connection, is connected to the angle probe in such a way that the second holder follows the two-dimensional displacement of said probe across the surface of the body on the same predetermined scale.

When both the recording material and the indicating units are separated from the body to be examined in this way, there is obtained, among other things, the advantage that these relatively vulnerable elements can be better protected against shocks, humidity and fouling during the scanning of the body.

A further development of this remote recording system, in which the recording material is replaced by the fluorescent screen of a conventional cathode ray tube, the apparatus is characterized in that the angle probe is mounted in a displaceable holding device which, moreover, is rigidly connected with the examined body, in such a way that it is possible to turn and move the probe unimpededly in a two-dimensional displacement across the surface of the body, in addition to which the holding device, in a manner known per se, is provided with position transducers that, via electronic control circuits, are connected to the cathode ray tube in such a way that its electron beam at all times follows a rectilinear track on the screen which, on a predetermined scale, reproduces the position of the probe in relation to the body and the direction of the projection of the sound path on the surface of the body, in addition to which the ultrasonic apparatus, in a manner likewise known per se, via electronic control circuits and intensity modulation circuits, is connected to the cathode ray tube in such a way that its electron beam produces a luminous point on the screen when the probe receives a reflected sound pulse and at a distance from the point on the screen that corresponds to the position of the probe, which distance, on the same predetermined scale, is proportional to the time interval that has elapsed from the emission to the reception of the sound pulse.

A particularly expedient embodiment of the apparatus employing the same cathode ray tube is characterized in that two rectilinear microphones are mounted at right angles to each other above the surface of the examined body and parallel to same, and in that, in rigid connection with the ultrasonic angle probe, two substantially punctiform sound sources are mounted for emitting spherical sound waves, one of them immediately above the sound emission point of the ultrasonic probe and the other at a distance herefrom immediately above the projection of the sound path on the surface of the body, in addition to which the two rectilinear microphones and the two punctiform sound sources, via coordinate registration circuits and electronic control circuits, are connected to the cathode ray tube in such a way that the time intervals from the emission to the reception of the spherical sound waves are converted into such control voltages that the electron beam of the tube at all times follows a rectilinear track on the screen which, on a predetermined scale, reproduces the position of the probe in relation to the body and the direction of the projection of the sound path on the surface of the body, in addition to which the ultrasonic apparatus, in a manner likewise known per se, via electronic control circuits and intensity modulation circuits, is connected to the cathode ray tube in such a way that its electron beam produces a luminous point on the screen when the probe receives a reflected sound pulse and at a distance from the point on the screen which corresponds to the position of the probe which distance on the same predetermined scale is proportional to the time interval that has elapsed from the emission to the reception of the sound pulse.

In these embodiments a purely electronic and more reliable recording is achieved without any mechanical indicating units and associated guiding means and, by means of the last embodiment, the additional, substantial advantage is gained that the position determination of the ultrasonic probe now can also take place by purely acoustic-electronic means and with a high degree of reliability without mechanical transmission means of any kind.

The embodiments described of the apparatus according to the invention are based on the prior art systems for ultrasonic examination and electronic transmission and recording of measuring results in general and have, for this reason, to be regarded as nothing more than illustrative examples of the many systems, which it will be obvious to a person skilled in the art to employ when constructing apparatuses for recording projection images according to the fundamental directions provided by the invention. Thus, this likewise applies to a possible employment of the prior art systems for temporary or permanent electric, electronic or magnetic storage of the produced measuring data etc. with a view to a desired reading or recreating of the projection images at a later date.

Figure 2:
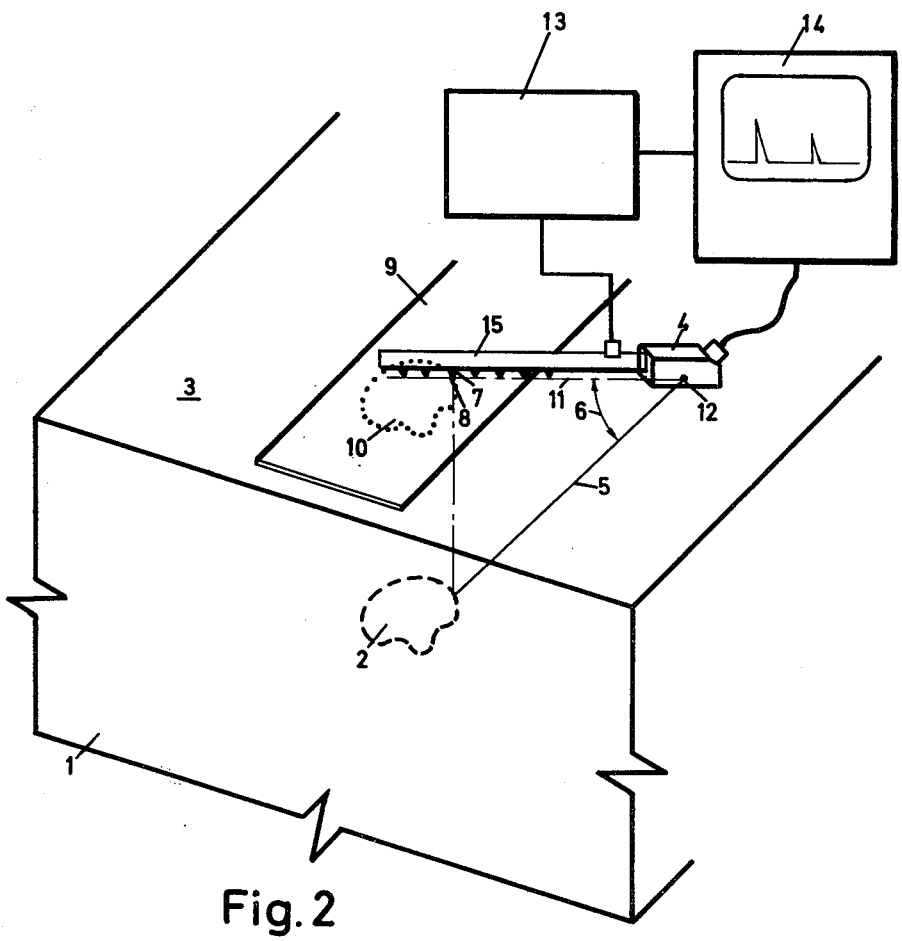
Figure 3:
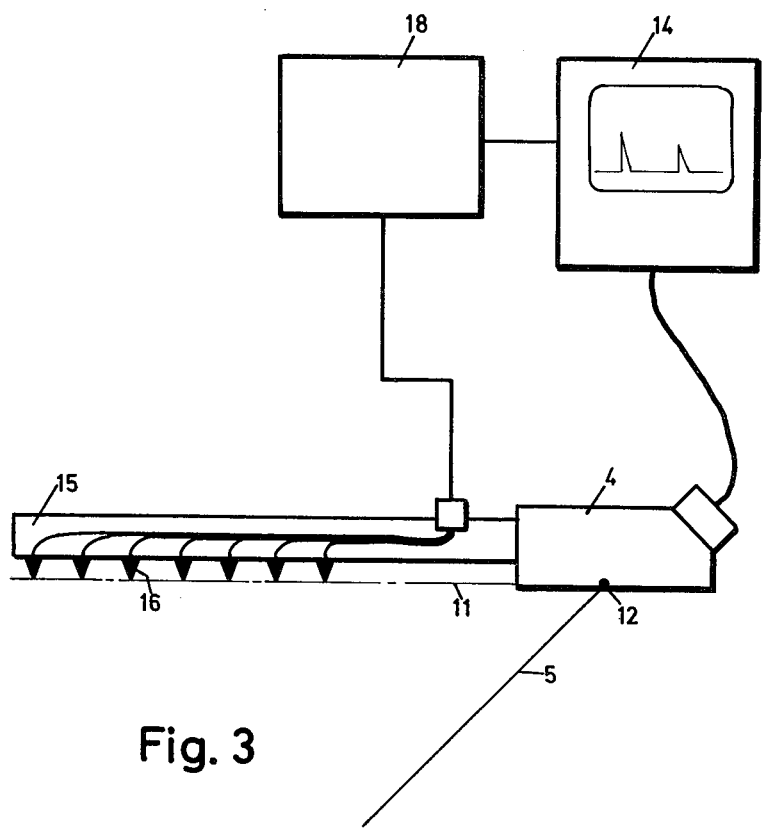
Figure 4:
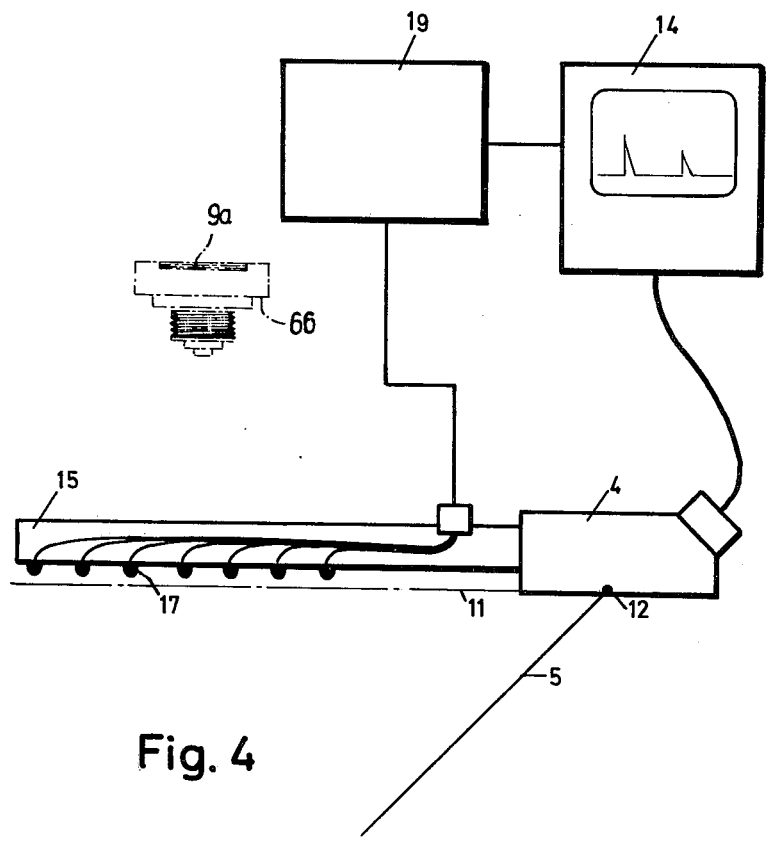
Figure 5:
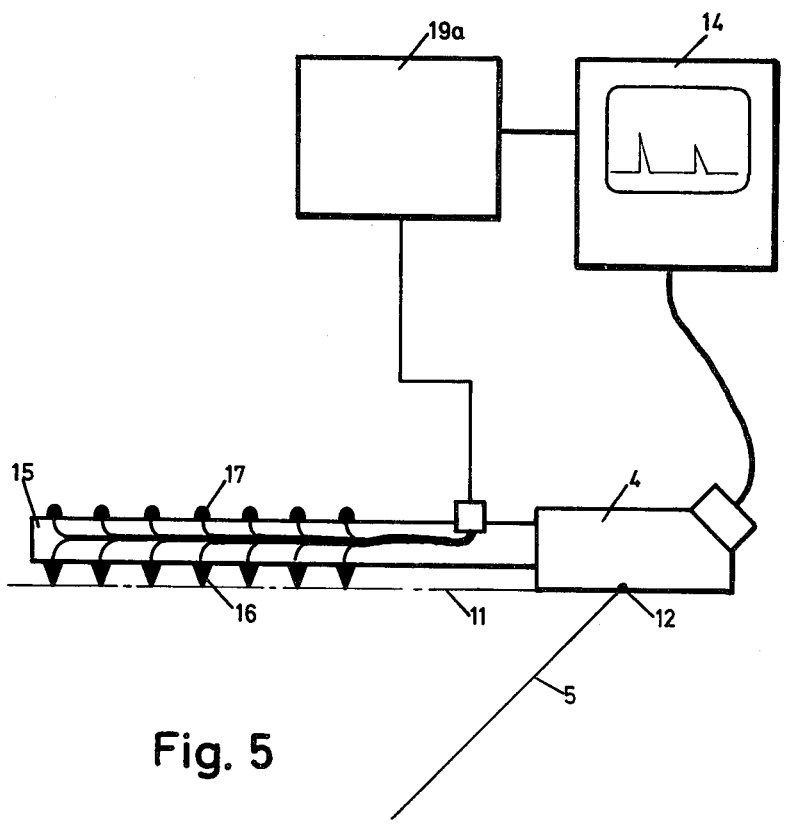
Figure 6:
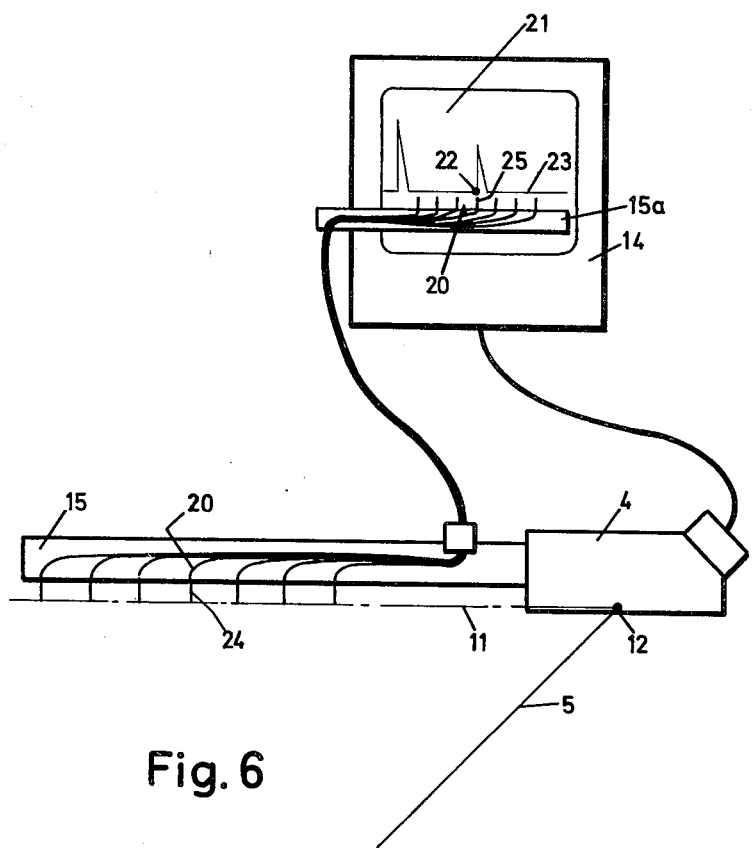
Figure 7:
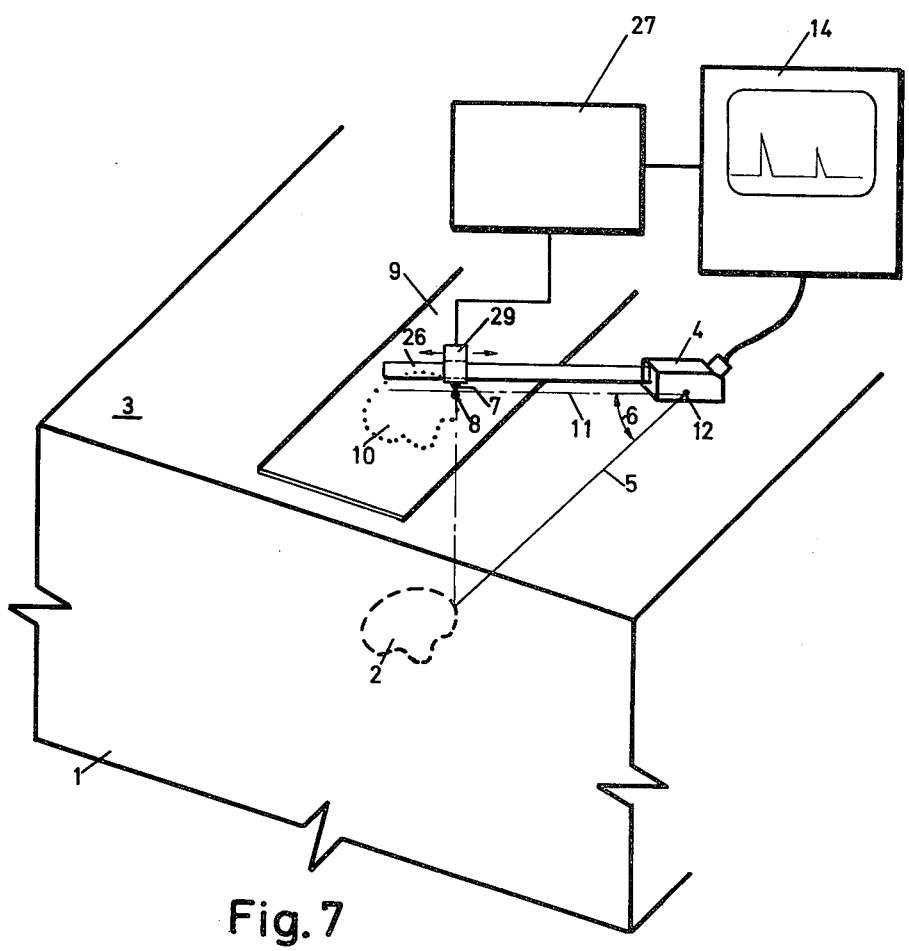
Figure 8:
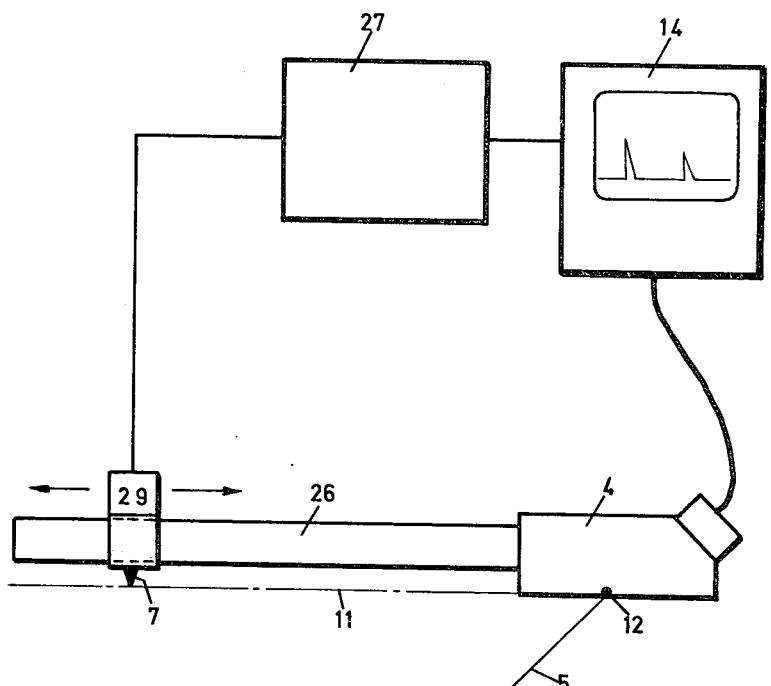
Figure 9:
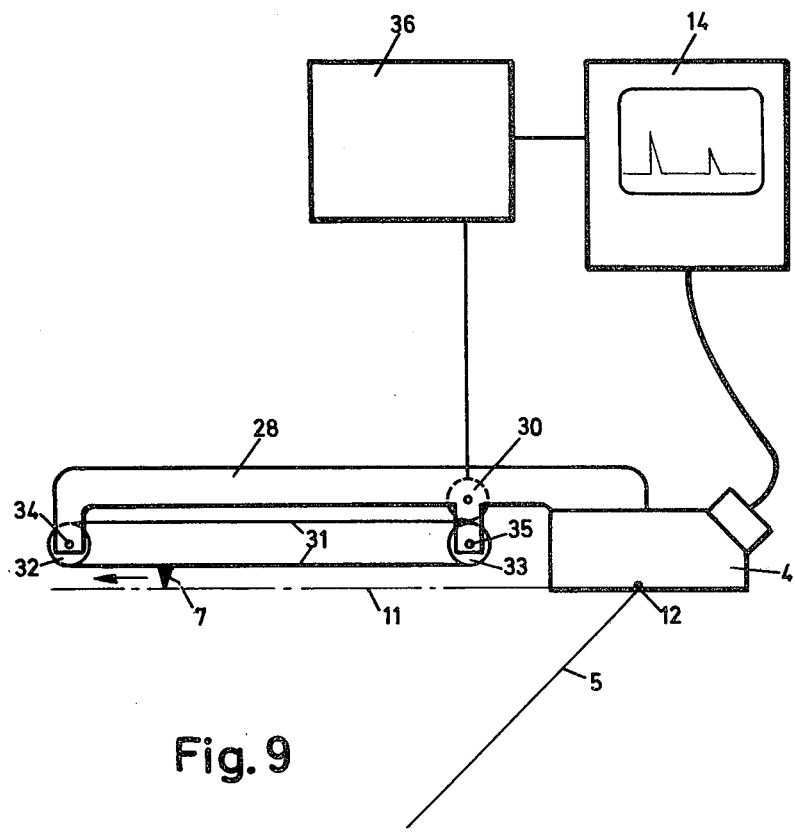
Figure 10:
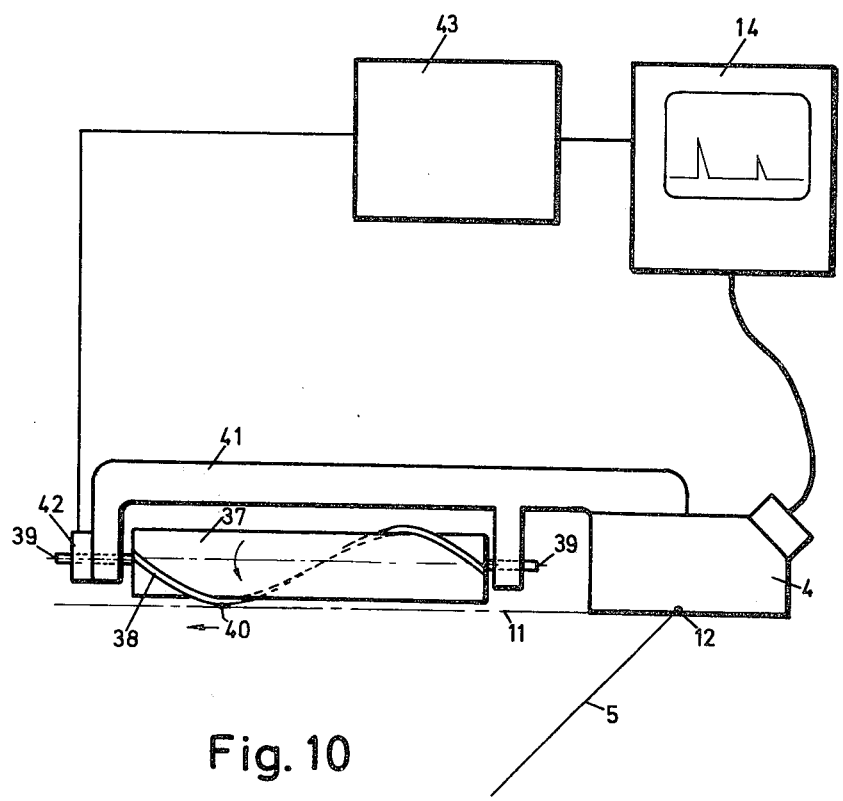
Figure 11:
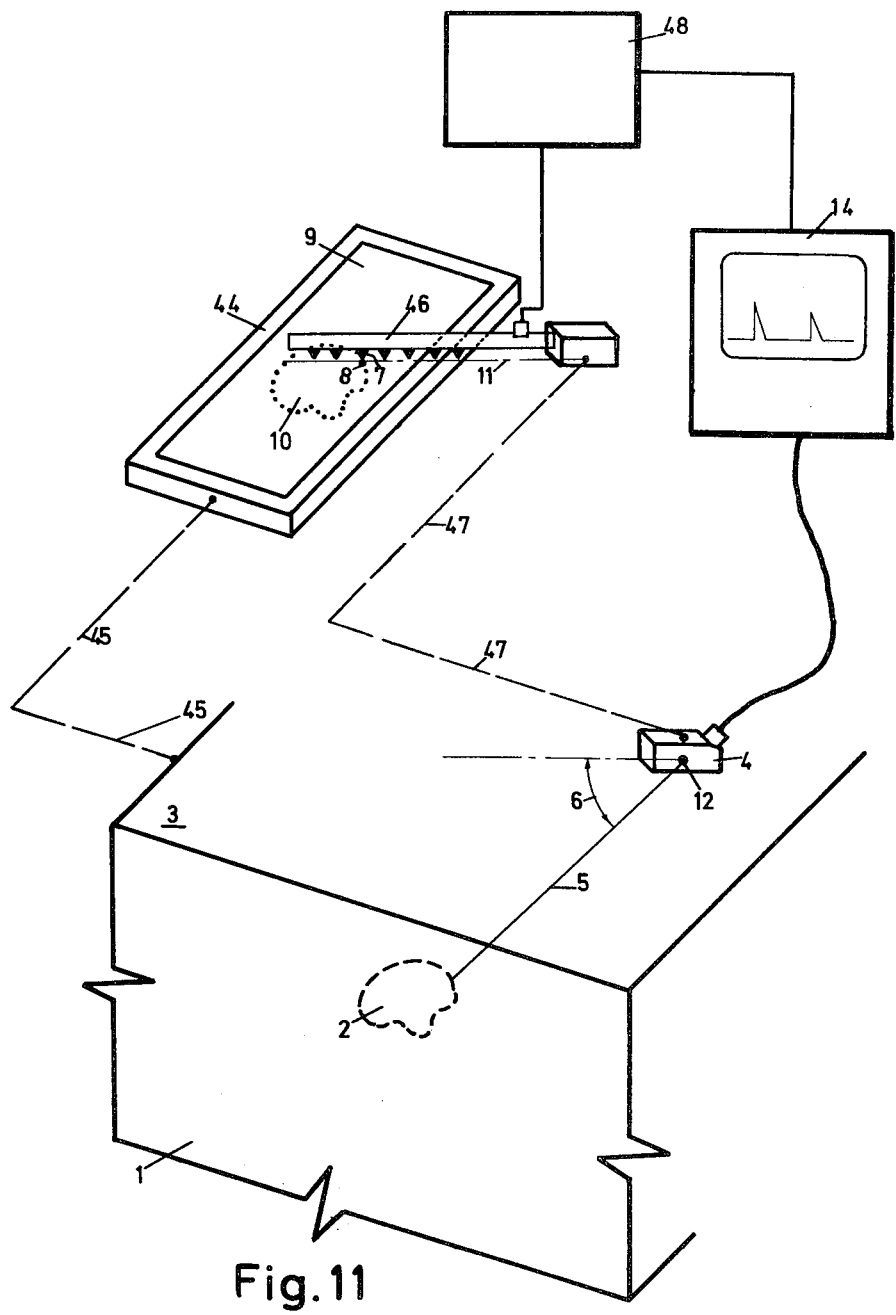
Figure 12:
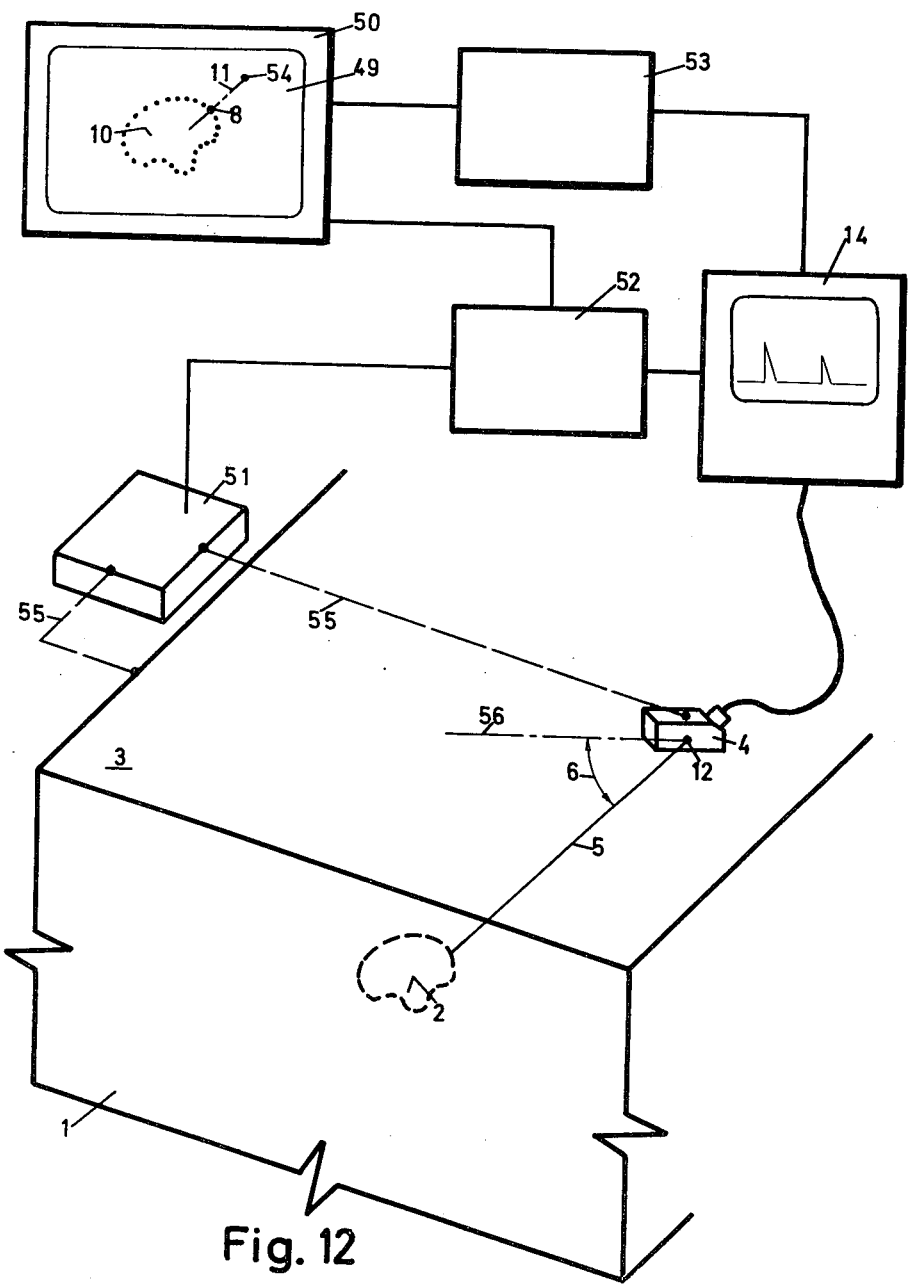
Figure 13:
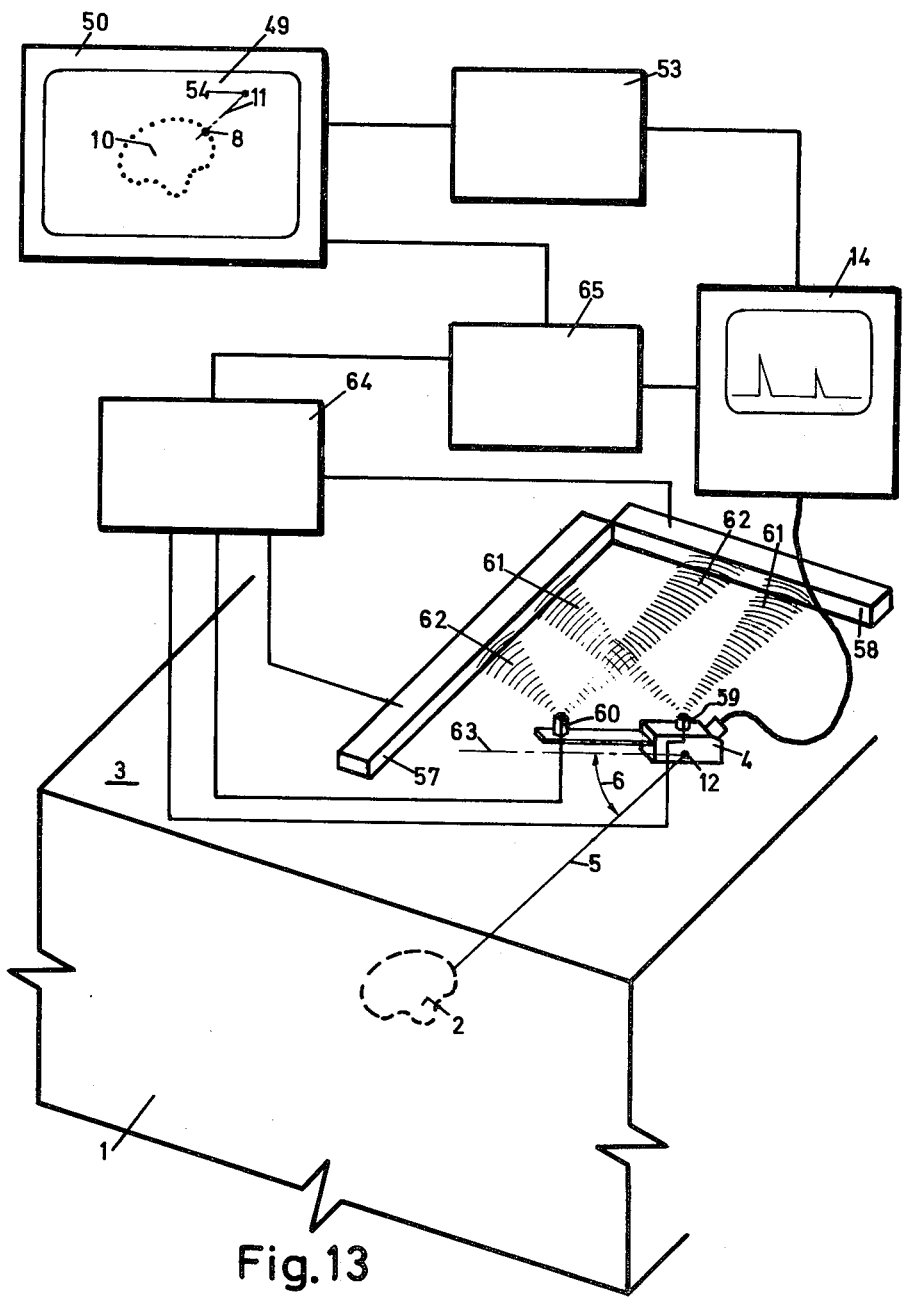

Below, the invention is described in greater detail with reference to the accompanying diagrammatical drawings, in which FIG. 1 shows diagrammatically and in perspective view the principle of the method of recording projection images, FIG. 2 shows diagrammatically and in perspective view the principle of the method when employing a line of indicating units, FIG. 3 shows diagrammatically the associated apparatus provided with conventional styluses, FIG. 4 shows diagrammatically the associated apparatus provided with conventional light diodes, FIG. 5 shows diagrammatically the associated apparatus provided with both styluses and light diodes, FIG. 6 shows diagrammatically the associated apparatus provided with conventional flexible light conductors, FIG. 7 shows diagrammatically and in perspective view the principle of the method when a single, movable indicating unit is employed, FIG. 8 shows diagrammatically the associated apparatus provided with a single, displaceable indicating unit, FIG. 9 shows diagrammatically the associated apparatus with the indicating unit mounted on an endless belt, FIG. 10 shows diagrammatically the associated apparatus provided with a conventional facsimile registration device, FIG. 11 shows diagrammatically and in perspective view the principle of the method when a mechanical-electronic remote recording of projection images is being employed, FIG. 12 shows diagrammatically and in perspective view the principle of the method when a mechanical-electronic remote recording on the screen of a cathode ray tube is being employed, and FIG. 13 shows diagrammatically and in perspective view the principle of the method when an acoustic-electronic remote recording on the screen of a cathode ray tube is being employed.

FIG. 1 shows a homogeneous body 1 with a plane surface 3 that is being scanned with a conventional angle probe 4 which, from a sound emission point 12, sends ultrasonic pulses into the body 1 in a direction 5 which forms a fixed angle 6 to the surface 3 of the body. A recording surface consisting of a plane recording material 9 is placed immediately above and parallel to the surface 3 of the body and in rigid connection with it. An internal inhomogeneity 2 in the body reflects ultrasonic pulses back in the direction 5 to the probe 4, where they, in a conventional manner, are converted into electric signals that are conducted to an ultrasonic apparatus (not shown). A conventional indicating means 7 produces a punctiform marking 8 on the recording material 9 along the axis of indication 11 that passes through the sound emission point 12 and has a direction that is coincident with the projection of the sound path 5 on the surface of the body.

Furthermore, FIG. 1 shows another, later position 4' of the probe in which, from the sound emission point 12', ultrasonic pulses are sent in the direction 5', and in which an indicating means 7' produces a punctiform marking 8' on the recording material 9 along the axis of indication 11' which passes through the sound emission point 12' in a direction that is coincident with the projection of the sound path 5' on the surface 3 of the body.

The punctiform markings produced by the examination as a whole form, in their entirety, a two-dimensional projection image 10 on the recording material 9 of the internal inhomogeneity 2 in the body 1.

The method according to the invention is carried out in conformity with the fundamental directions as detailed below.

The angle probe 4 is guided across the plane surface 3 of the body and is hereby made to assume a large number of positions and directions in relation to this surface while continually emitting a great number of short-duration ultrasonic pulses in a direction that is stationary in relation to the probe and which, at all times, forms a predetermined, fixed angle 6 with the surface 3 of the body.

One or several conventional fixed or displaceable indicating units 7 which, by being electrically activated, appear as luminous points or produce punctiform markings 8, are mounted in a marking position in relation to the plane recording material and are connected in a manner known per se to the angle probe in such a way that the marking is at all times made along an axis of indication 11 that follows the two-dimensional displacement of the probe 4 across the surface 3 of the body, which axis of indication 11 passes through the sound emission point 12 of the probe in a direction which is at all times coincident with the projection of the sound path 5 on the surface 3 of the body.

Furthermore, the indicating means 7 are connected to the probe 4 in a manner likewise known per se, as well as to the electronic circuits of a conventional ultrasonic apparatus in such a way that a marking 8 is activated on the registration material 9 when the probe 4 receives a reflected sound pulse from an internal inhomogeneity 2 in the body 1 and at a distance from the sound emission point 12 that is proportional to the time interval that has elapsed from the emission to the reception of the sound pulse.

By the special, fundamental combination according to the invention of employing a registration material 9 that follows the body 1 and an axis of indication 11 which, at all times, follows the probe 4 while, at the same time, causing the reflected sound pulses to produce punctiform markings 8 at distances from the sound emission point 12 which, for each individual sound pulse, is proportional to the time interval in which the sound pulse has moved at constant speed from the sound emission point 12 to a point of reflection at an internal inhomogeneity 2 and back to the sound emission point 12, precisely that desired result is obtained which constitutes the object of the invention, that is to say that the punctiform markings 8 successively produced during the entire examination gradually coalesce so as to form a two-dimensional projection image 10 on the recording material 9 of the internal inhomogeneity 2 in the body 1.

The proportionality factor between the distance from the sound emission point 12 to the associated punctiform marking 8 and the measured time interval from the emission to the reception of a sound pulse can be selected according to the type of the desired form of reproduction.

If the proportionality factor is selected to be half the product of the speed of sound in the material of the examined body and cosine to the angle 6, the projection image 10 will be a correct reproduction in true dimension of the projection of the internal inhomogeneity 2 on the surface 3 of the body.

If the proportionality factor is additionally multiplied with a larger or smaller correction factor, and the same correction factor is used as a ratio of transformation in the movement of the recording material 9 in relation to the movement of the body 1 and in the movement of the axis of indication 11 in relation to the displacement of the probe 4, it will be possible to produce at will correctly reproduced, enlarged or reduced projection images of the internal inhomogeneities of the body.

If the body is examined only with the probe 4 secured parallel to a specific direction in relation to the surface 3 of the body, it will be possible, in a corresponding fashion, by selecting a greater or smaller proportionality factor, to produce at will correctly reproduced projection images in which the dimensions of the internal inhomogeneities are reproduced as desired enlarged or reduced only in the direction in question.

From the fundamental directions provided by the invention, an expert who is familiar with the prior art of ultrasonic testing and the transmission and recording of measuring results in general, will, moreover, be able to carry out the method in practice in many different and immediately obvious ways and by employing the conventional supplementary means of the prior art.

As illustrative but not at all exhaustive examples of the practical performance of the fundamental method provided according to the invention, a number of particularly expedient embodiment examples of the method according to the invention are described in the following.

FIG. 2 shows a solid body 1 with a plane surface 3 that is being scanned with an angle probe 4 which, from a sound emission point, sends ultrasonic pulses into the body 1 in a direction 5 which forms a fixed angle 6 to the surface 3 of the body. A plane recording material 9 is placed immediately above and parallel to the surface 3 of the body and in rigid connection with it. An internal inhomogeneity 2 in the body reflects the sound pulses back in the direction 5 of the probe 4 where, in a conventional manner, they are converted into electric signals that are conducted to a conventional ultrasonic apparatus 14. A line of conventional indicating units 7 are mounted in a holder 15 at fixed intervals along the axis of indication 11 and in rigid connection with the probe 4. Each individual indicating unit 7 is mounted in a marking position in relation to the recording material 9 and is, via electronic control circuits 13, connected to the receiving part of the ultrasonic apparatus 14. During the scanning of the body 1, the indicating units 7 produce markings 8 on the recording material 9.

The method according to the invention is carried out in the manner illustrated in FIG. 2 in conformity with the directions detailed below.

The angle probe 4 is guided across the plane surface 3 of the body and is hereby made to assume a large variety of positions and directions in relation to it, whereby the indicating units 7 are simultaneously guided across the recording material 9.

Each individual indicating unit 7 is connected in a generally known manner via conventional electronic control circuits 13 to the ultrasonic apparatus 14 in such a way that the indicating unit 7 is activated and produces a punctiform marking 8 on the recording material 9 when and only when a signal is generated from a reflected sound pulse, the total time taken by which for forward and return travel in the body 1 is proportional in a specific, predetermined relationship to the distance from the sound emission point 12 of the probe to the indicating unit 7 in question.

By the fundamental method thus indicated, the punctiform markings 8 produced successively during the entire examination will gradually coalesce so as to form a two-dimensional projection image 10 on the recording material of the internal inhomogeneity 2 in the body 1.

In principle, any type of prior art indicating unit may be employed as indicating unit 7 that is capable of being activated electrically in order to appear in the form of luminous points or to produce punctiform markings on an associated conventional recording material.

FIG. 3 thus illustrates schematically the employment of conventional styluses 16 which, for example, may be spark recorders that produce markings on an associated, electrosensitive recording material when they are activated via associated conventional electronic control circuits 18.

FIG. 4 illustrates correspondingly schematically the employment of substantially punctiform light diodes 17, which by activation via associated electronic control circuits 19, appear as luminous points and thereby produce punctiform markings on an associated photosensitive recording material which, for instance, may be conventional photographic paper or a conventional photographic film and may possibly be placed in a photographic camera 66 with open shutter.

FIG. 5 illustrates correspondingly schematically the employment of conventional styluses 16 where, above each stylus 16, on the side of the holder 15 that is facing away from the surface of the body, a conventional light diode 17 is additionally employed which, via associated conventional electronic control circuits 19a, is activated simultaneously with the stylus 16 in question.

A visual indication is hereby produced every time a permanent marking is produced on the recording material, constituting a substantial aid to the operator.

FIG. 6 illustrates correspondingly schematically the employment of a bundle of conventional, flexible light conductors 20 each having a substantially punctiform cross section, and the first end 24 of which, in a holder 15, is arranged at the axis of indication 11, and the second end 25 of which, in a holder 15a, is arranged immediately in front of and facing the screen 21 of the cathode ray tube of a conventional ultrasonic testing apparatus 14 at a distance along the time deflection axis 23 of the screen that is proportional to the distance from the sound emission point 12 of the probe to the first end 24 of the light conductor. Video signals from the reflected sound pulses produce luminous points or dashes 22 along the time deflection axis on the screen 21 of the cathode ray tube.

The method according to this embodiment of the invention is carried out in the way that a sound pulse reflected to the probe 4 is, in a conventional manner, made to produce a luminous point or a luminous dash 22 on the screen 21 of the cathode ray tube at a distance along the time deflection axis 23 of the screen that is proportional to the total time taken by the forward and return travel of the sound pulse in the examined body 1 (normal so-called A-scan). The light of this marking 22 on the screen 21 is transmitted directly via the light conductor 20 having its second end 25 mounted opposite to the marking 22 to the first end 24 of the light conductor and here produces a corresponding marking 8 on a photosensitive recording material 9 at the desired distance from the sound emission point 12 of the probe.

FIG. 7 ilustrates schematically the principle of the method according to the invention in an expedient embodiment in which the punctiform markings 8 are produced by an indicating unit 7 that is displaceably mounted in a holder 26 in rigid connection with the probe 4 in such a way that the indicating unit 7 is able to execute a movement along the axis of indication 11. Indicating unit 7 is, via a conventional position trancducer 29 which establishes it actual distance from the sound emission point 12 and electronic control circuit 27, connected to the receiver of the ultrasonic apparatus 14.

The method according to this embodiment of the invention is carried out in the way illustrated in FIG. 7 that the indicating unit 7, during the scanning of the body 1 is made to execute a continually repeated movement along the axis of indication 11. This movement can be effected manually or by a mechanical driving device (not shown) incorporated into the holder 26.

The indicating unit 7 is connected in a generally known manner via the position transducer 29 and via conventional electronic circuits 27 to the ultrasonic apparatus 14 in such a way that the indicating unit 7 is activated and produces a punctiform marking 8 on the registration material 9 when and only when a signal is generated from a reflected sound pulse, the total time taken by which in forward and return travel is proportional, in a specific, predetermined relationship to the distance from the sound emission point 12, to the point where the indicating unit happens to be when the sound pulse is received.

In the course of a conventional ultrasonic examination, the probe 4 continually emits ultrasonic pulses at a rate of 500 to 1,000 pulses per second. These pulses travel through the body at a very high speed and their projections on the axis of indication 11 thus pass the indicating unit 7 a great many times every second. If only the indicating unit 7 is made to pass along the axis of indication at least once for each position of the probe 4, there will thus be ample time in order to obtain with certainty at least one coincidence of the position of the indicating unit with the position of a reflected sound pulse when the indicating unit 7 in the course of its movement reaches the point on the axis of indication 11 where activation is desired for a marking 8 to be produced on the recording material 9.

By means of the fundamental method thus indicated, the punctiform markings 8 produced successively during the entire examination will gradually coalesce so as to form a two-dimensional projection image 10 on the recording material 9 of the internal inhomogeneity 2 in the body 1.

It is possible in a principle to employ any known type of indicating units 7, including also the styluses, light diodes and flexible light conductors dealt with in connection with FIGS. 3-6.

FIG. 8 thus shows schematically the employment of such an indicating unit 7 which is made to execute a continually repeated, reciprocating movement along the axis of indication 11.

FIG. 9 shows correspondingly schematically the employment of such an indicating unit 7 mounted in rigid connection to an endless belt 31 that is made to pass around two rollers 32 and 33 whose shafts 34 and 35 are mounted in rigid connection with the probe 4 parallel to the recording material 9 and at right angles to the axis of indication 11. The indicating unit 7 is hereby made to execute a continually repeated movement in the same direction along the axis of indication 11.

FIG. 10 shows correspondingly schematically the employment of a displaceable indicating unit in the form of a conventional facsimile registration device consisting of a cylinder 37 provided with a helical projection 38 and made to rotate around a shaft 39 that is mounted in rigid connection with the probe 4 parallel to the axis of indication 11. The point of contact 40 between the helical projection 38 and the recording material 9 is hereby made to execute a continually repeated movement in the same direction along the axis of indication 11. The indicating device is activated in a generally known manner by an electric spark being produced between the helical projection 38 and an electrosensitive recording material 9, whereby a marking is produced on it at the point of contact 40.

FIG. 11 illustrates schematically the principle of the method according to the invention in an expedient embodiment in which a recording material 9 is separated from the examined body 1 and arranged in a first holding device 44 which, via a first mechanical or electrial connection 45, is connected to the body 1. The indicating units 7 are mounted in the conventional marking position in relation to the registration material 9 along an axis of indication 11 in a second holding device 46 which, via a second conventional, mechanical or electrical connection 47, is connected to the probe 4. The probe 4 is, in a conventional manner, connected to a conventional ultrasonic apparatus 14 and the indicating units 7 are, likewise via electronic control circuits 48, connected to the receiving part of the ultrasonic apparatus 14. During the scanning of the body 1, the indicating units 7 produce punctiform markings 8 on the recording material 9.

The method according to embodiment of the invention illustrated in FIG. 11 is carried out in the way that the probe 4 is guided across the plane surface 3 of the body and is hereby made to assume a large variety of positions and directions in relation to same while, at the same time, in a manner generally known, the holder via connection 47, is made to follow on a predetermined scale the two-dimensional displacement of the probe 4 across the surface 3 of the body and thereby conducts the indicating units 7 across the recording material 9 in such a way that the axis of indication 11 at all times represents the projection of the sound path 5 on the surface 3 of the body and so that the reference point on the axis of indication 11 at all times represents the sound emission point 12.

If the body 1 remains stationary during the scanning operation, it is possible to employ a fixed holding device 44. If the body is moved during the scanning operation, the holding device 44, in a generally known manner, via connection 45, is on the predetermined scale made to follow the movement of the body in the plane that is constituted by the surface 3 of the body. The relative movement of the body 1 and the probe 4 will hereby be correctly transmitted and reproduced.

Each of the indicating units 7 is connected in quite the same manner as in the previously described embodiments of the method according to the invention via conventional electronic control circuits 48 to the ultrasonic apparatus 14 in such a way that, on the preselected scale, punctiform markings 8 are produced at the desired, correct distances from the reference point on the axis of indication 11.

By means of the fundamental method thus indicated, the punctiform markings 8 produced during the entire examination will gradually coalesce so as to form on the preselected scale a two-dimensional projection image 10 of the internal inhomogeneity 2 in the body 1 by remote registration on the registration material 9.

FIG. 12 illustrates schematically the principle of the method according to the invention in an expedient development of the embodiment shown in FIG. 11 incorporating remote recording. Here, the fluorescent screen 49 of a conventional cathode ray tube 50 is employed as recording material and an electron beam controlled in a conventional manner is used as indication means, which beam, by means of intensity modulation, produces luminous points on the screen 49. The probe 4 is connected to the body 1 via a conventional mechanical or electrical connection 55 which, via a system of position transducers 51 and electronic circuits 52, is again connected to the cathode ray tube 50. The probe 4 is connected in a conventional manner to a conventional ultrasonic apparatus 14 which, again via the electronic control circuits 52 and the intensity modulation circuits 53, is connected to the cathode ray tube 50.

The method according to the invention is carried out in the fashion illustrated in FIG. 12 as per the below-detailed directions.

The probe 4 is guided across the plane surface 3 of the body and it is hereby made to assume a great variety of positions and directions in relation to same.

By means of a generally known mechanical or electrical connection 55, the two-dimensional displacement and the direction of the probe 4 is, in a manner known per se, converted via a conventional system of position transducers 51 and associated conventional electronic control circuits 52, into such control voltages for the electron beam of the cathode ray tube 50 that the electron beam sweep of the cathode ray tube takes place along a rectilinear track 11 on the screen 49 the direction of which constitutes the axis of indication and which follows the projection 56 of the sound path 5 on the surface 3 of the body and with a starting point 54 which follows the sound emission point 12.

At the same time, the video signal generated by the reception of a reflected sound pulse and the associated deflection voltage are employed in a manner likewise known per se, via conventional intensity modulation circuits 53 and electronic control circuits 52, respectively, in order to produce a luminous point 8 on the axis of indication 11 when the probe 4 receives a reflected sound pulse, at a distance from the reference point 54 of the axis of indication which, on the same predetermined scale, is proportional to the time interval that has elapsed from the emission to the reception of the sound pulse.

A conventional screen having a short afterglow period can be employed as screen 49 in the cathode ray tube. In this case, the short-duration luminous points 8 are photographed by means of a photographic camera whose shutter is kept open during the entire scanning period of the body 1.

It is also possible to employ as screen 49 a conventional screen with a long afterglow period or a conventional, electronically controlled storage screen, which preserves the markings 8 produced in the form of luminous dots during the entire scanning period of the body 1, following which the total screen image produced at the termination of the scanning operation can, if so desired, be photographed as a permanent documentation of the result of the testing operation.

By means of the fundamental method thus indicated, the punctiform markings 8 successively produced during the entire testing operation will gradually coalesce so as to form a two-dimensional projection image 10 on the preselected scale by remote recording of the internal inhomogeneity 2 of the body 1 on the screen 49.

FIG. 13 shows schematically the principle of the method according to the invention in a particularly expedient development of the embodiment shown in FIG. 12 incorporating remote recording on the screen of a cathode ray tube, in this case with simultaneous utilization of the prior art for acoustic-electronic position determination and coordinate reading.

Immediately above the plane surface 3 of the body, two conventional, rectilinear microphones 57 and 58 are mounted at right angles to each other and parallel to the surface 3. Two substantially punctiform sound sources 59 and 60 are mounted rigidly connected to the probe 4, one of them 59 immediately above the sound emission point 12 and the other a short distance herefrom immediately above the projection 63 of the sound path 5 on the surface 3 of the body 1. The two rectilinear microphones 57 and 58 are, via the coordinate registration circuit 64 and electronic control circuits 65, connected to the cathode ray tube 50. The probe 4 is, in a conventional manner, connected to a conventional ultrasonic apparatus 14 which, again via the electronic control circuits 65 and the intensity modulation circuits 53, is connected to the cathode ray tube 50.

The method according to the invention is carried out in the fashion illustrated in FIG. 13 in conformity with the instructions detailed below.

The ultrasonic probe 4 is guided across the plane surface 3 of the body and it is hereby made to assume a great variety of positions and directions in relation to it.

The two punctiform sound sources 59 and 60, which expediently can be quite short electric spark gaps, are made to emit alternately and at short time intervals short-duration, spherical sound waves 61 and 62 that are a little later picked up and registered by the two rectilinear microphones.

The four time intervals from the emission to the reception of the spherical sound waves 61 and 62 which are proportional to the perpendicular distances from the sound sources 59 and 60 to the rectilinear microphones 57 and 58, are, in a manner known per se, via conventional coordinate registration circuits 64 and conventional electronic control circuits 65, converted into such control voltages for the electron beam of the cathode ray tube 50 that electron beam sweep takes place along a rectilinear track 11 on the screen 49 which constitutes an axis of indication 11 and the direction of which follows the projection 63 of the sound path 5 on the surface 3 of the body, and with a starting point 54 which follows the ultrasonic sound emission point 12.

The production of the punctiform markings 8 and, thereby, of the correct projection image 10 on the screen 49 is subsequently effected in quite the same fashion as described in the foregoing in the text relating to FIG. 12.

An apparatus to be employed when carrying out the method according to the invention in connection with a conventional ultrasonic apparatus 14 and a conventional recording material 9 mounted immediately above and parallel to the surface 3 of the examined body and in rigid connection therewith, is shown schematically in FIG. 2 and the components of the apparatus, its principal design and mode of operation are described in the foregoing in the text relating to FIG. 2.

A first expedient embodiment of the apparatus in which conventional styluses 16 and associated, conventional electronic control circuits 18 are employed, is illustrated diagrammatically in FIG. 3 and described in the foregoing in the text covering this FIGURE.

A second expedient embodiment of the apparatus in which conventional, substantially punctiform light diodes 17 and associated conventional electronic circuits 19 are employed, is shown diagrammatically in FIG. 4 and is described in the foregoing in the text pertaining to this FIGURE.

A third expedient embodiment of the apparatus in which both conventional styluses 16 and conventional light diodes 17 as well as associated, conventional electronic control circuits 19a are simultaneously employed, is shown schematically in FIG. 5 and is described in the foregoing in the text relating to this figure.

A fourth expedient embodiment of the apparatus in which a bundle of conventional, flexible light conductors 20 each having a substantially punctiform cross-section are employed, is shown diagrammatically in FIG. 6 and is described in the foregoing in the text relating to this figure.

In yet another expedient embodiment of the apparatus in which a conventional indicating unit 7 that is displaceably mounted in a holder 26 and an associated, conventional position transducer 29, as well as associated, conventional electronic control circuits 27 are used, is shown diagrammatically in FIGS. 7 and 8 and is described in the foregoing in the text pertaining to this figure.

A special embodiment of this apparatus in which a conventional indicating unit 7 that is rigidly connected to an endless belt 31 mounted in a holder 28, and an associated, conventional position transducer 30, as well as associated, conventional electronic control circuits 36 are employed, is shown schematically in FIG. 9 and is described in the foregoing in the text relating to this figure.

A second special embodiment of this apparatus in which a conventional facsimile registration device 37, 38 is employed mounted in a holder 41 and an associated, conventional position transducer 42, as well as associated, conventional electronic circuits 43 are used, is shown diagrammatically in FIG. 10 and is described in the foregoing in the text covering this figure.

A further expedient embodiment of the apparatus according to the invention in which the recording material 9 and the indicating units 7 are mounted separated from the examined body 1 and from the probe 4 and mounted in special holding devices 44 and 46 connected to conventional mechanical or electrical connections 45 and 47, and in which conventional electronic control circuits 48 are used, is shown diagrammatically in FIG. 11 and is described in the foregoing in the text relating to this figure.

Yet another further developed embodiment of this remote recording system in which recording on a fluorescent screen 49 of a conventional cathode ray tube 50 and a conventional, mechanical or electrical connection 55 with an associated system of position transducer 51, as well as conventional electronic control circuits 52 and conventional intensity modulation circuits 53 are employed, is shown diagrammatically in FIG. 12 and is described in the foregoing in the text pertaining to this figure.

A particularly expedient embodiment of the apparatus incorporating the same cathode ray tube 50, and in which two conventional, rectilinear microphones 57 and 58 and two conventional, substantially punctiform sound sources 59 and 60 connected to associated, conventional coordinate registration circuits 64 and conventional electronic control circuits 65, as well as intensity modulation circuits 53 are employed, is shown diagrammatically in FIG. 13 and is described in the foregoing in the text pertaining to this figure.

In the embodiments of the apparatus according to the invention illustrated in the drawings and described in the foregoing it has not been deemed necessary or expedient to provide more detailed information regarding the design, construction and mode of operation of the individual components, apparatuses, connections and electronic circuits that have been shown diagrammatically. All these details form part of the prior art and are in daily use in practice. It is possible, moreover, to construct and combine them in many different ways which are well-known and obvious to the expert who is familiar with conventional ultrasonic examination, design of electronic circuits and transmission and recording of measuring data in general.

In order to obtain a true projection image, possibly enlarged or reduced, of the inhomogeneities, the axis of indication and its reference point must be displaced in such a way that their displacements across the recording surface can be derived from the movements across the surface of the body of the projection of the sound path on the surface of the body and the sound emission point of the probe, respectively, by a similitude transformation. In those cases where the reference point coincides with the sound emission point and the axis of indication is parallel to the projection of the sound path, the displacement part of the similitude transformation is zero. If the image formed is true to dimension in relation to the projection of the inhomogeneity on the surface of the body, the similitude ratio is equal to one.

We claim:

1. A method of indicating, or of recording images of internal inhomogeneities in otherwise homogeneous bodies which have a substantially plane or slightly curved surface, by ultrasonic examination according to the pulse echo method, including guiding at least one angle probe connected to an ultrasonic apparatus across the surface of the body to scan its interior by emitting and receiving short-duration ultrasonic pulses in directions that form a predetermined angle with the surface of the body, and activating indicating means in response to received reflected sound pulses to produce punctiform markings on a substantially plane recording surface, characterized by the steps of moving the indicating means having an axis of indication along which the markings on the recording surface are made to thereby move the axis in the plane of the recording surface in such a way that the displacement of a reference point on the axis of indication in relation to the recording surface follows the two-dimensional displacement of the sound emission point of the probe in relation to the surface of the body on a predetermined scale, the axis of indication in relation to the recording surface following the direction of the projection of the sound path on the surface of the body, each of said markings being effected at a distance from the reference point that is proportional to the time interval that has elapsed from the emission to the reception of a sound pulse.

2. A method as claimed in claim 1, characterized by the step of placing a recording material immediately above and parallel to the surface of the examined body and rigidly connected thereto, and rigidly connecting said indicating means to the probe in such a way that the axis of indication is coincident with the projection of the sound path on the recording material, and that the reference point is coincident with the sound emission point.

3. A method as claimed in claim 2, characterized by mounting at least one line of indicating units at fixed intervals along the axis of indication and in rigid connection with the probe, each of said indicating units being connected to the receiver part of the ultrasonic apparatus which is connected to said angle probe to emit and receive the ultrasonic pulses, and activating each of said indicating units when and only when a signal is generated from a reflected sound pulse, the distance from the sound emission point of the probe to the indicating unit being activated being proportional to the total time taken by said pulse for forward and return travel in the body.

4. A method as claimed in claim 3, characterized in that said indicating units are styluses activated electrically, and including the step of electrically activating said stylus to produce a punctiform marking on the associated recording material.

5. A method as claimed in claim 1, characterized by mounting at least one line of substantially punctiform light diodes as indicating units at fixed intervals and in rigid connection with the probe along a straight line which substantially coincides with the projection of the sound path on the surface of the body, connecting each individual light diode to the receiver part of the ultrasonic apparatus, activating the individual light diode to appear as a luminous point when and only when a signal is generated from a reflected sound pulse, the distance from the sound emission point of the probe to the one of the light diodes being activated being proportional to the total time taken by said pulse for forward and return travel in the body.

6. A method as claimed in claim 5, characterized by the step of producing punctiform markings on a photosensitive recording material placed immediately above and parallel to the surface of the examined body and rigidly connected thereto in response to activation of said light diodes.

7. A method as claimed in claim 5, characterized by the step of producing the punctiform markings on a photosensitive recording material placed above and parallel to the surface of the examined body in a stationary photographic camera whose shutter is open.

8. A method as claimed in claim 4, characterized by the step of mounting above each stylus and on the side that is facing away from the surface of the body, a substantially punctiform light diode that is activated simultaneously with the stylus and thereby provides a visual indication every time a marking is produced on the recording material.

9. A method as claimed in claim 3 including connecting with the ultrasonic apparatus, a cathode ray tube on the fluorescent screen of which video signals from the reflected sound pulses produce luminous points or dashes along a time deflection axis at distances which are proportional to the total time taken by the sound pulses for forward and return travel in the body, and producing a corresponding punctiform marking on the recording material comprising photosensitive material, by the steps of arranging flexible light conductors having a substantially punctiform cross-section as the indicating units, a first end of each of said light conductors being arranged on the axis of indication and facing a photosensitive recording material, and a second end being mounted immediately in front of and facing the screen of the cathode ray tube and at a distance along the time deflection axis of the screen that is proportional to the distance from the sound emission point of the probe to the first end of the light conductor, whereby a light marking on the screen opposite to the second end of the light conductor is transmitted via the light conductor and thereby produces a corresponding, punctiform marking on the photosensitive recording material at the surface of the body.

10. A method as claimed in claim 2, characterized by displaceably mounting at least one indicating unit in a holder that is in rigid connection with the probe, said indicating unit being connected via a position transducer to a receiver part of the ultrasonic apparatus so that the indicating unit is activated when and only when a signal is generated from a reflected sound pulse, the total time taken by said pulse in forward and return travel in the body under examination being proportional in a specific, predetermined relationship to the distance from the sound emission point of the probe to the location of the indicating unit when the sound pulse is received.

11. A method as claimed in claim 10, characterized in that said one indicating unit is executing a continually repeated reciprocating movement along the axis of indication.

12. A method as claimed in claim 10, characterized in that said one indicating unit is mounted in rigid connection with an endless belt running around two rollers, the shafts of which are rigidly connected to the probe and are mounted parallel to the recording material and perpendicular to the axis of indication, whereby the indicating unit is made to carry out a continually repeated movement in the same direction along the axis of indication.

13. A method as claimed in claim 10, characterized in that a facsimile registration device is employed as indicating unit (7), which device consists of a cylinder (37) provided with a helical projection (38) and rotating around a shaft (39) which is rigidly connected to the probe (4) and is mounted parallel to the axis of indication (11), whereby the point of contact (40) between the helical projection (38) and the recording material (9) is made to execute a continually repeated movement in the same direction along the axis of indication (11).

14. A method as claimed in claim 1, characterized by mounting the recording material separated from the examined body in a first holding device which is connected to the body to represent the plane position of the body, and mounting the indicating units in relation to the recording material along the axis of indication in a second holding device which, via a second mechanical or electrical connection, is connected to the probe to represent the position of the probe on the body.

15. A method as claimed in claim 1, characterized in that a fluorescent screen of a cathode ray tube comprises the recording surface and a controlled electron beam comprises the indicating means, and comprises the steps of converting dimensional displacement of the probe across the surface of the body into control voltages for the electron beam sweep in the cathode ray tube such that the sweep follows a rectilinear track on the screen which constitutes the axis of indication, and producing a luminous point on the axis of indication in response to video signals and associated deflection voltages produced in the ultrasonic apparatus by the reception of a reflected sound pulse when the probe receives the reflected sound pulse and at a distance from the reference point on the axis of indication which, on the same predetermined scale, is proportional to the time interval that has elapsed from the emission to the reception of the sound pulse.

16. A method as claimed in claim 15, characterized by determining the actual position and direction of the probe in relation to the surface of the body by mounting two rectilinear microphones at right angles to each other immediately above and parallel to the surface of the body mounting in fixed connection with the ultrasonic probe two substantially punctiform sound sources for the emission of spherical sound waves, one of the sound sources being immediately above the sound emission point of the ultrasonic probe and the other sound source at a distance herefrom immediately above the projection of the sound path on the surface of the body, alternately and at brief time intervals, energizing said sound sources to emit short-duration, spherical sound waves, which time intervals are proportional to the perpendicular distances from the sound sources to the linear microphones and converting the received signals according to said proportion to locate and direct the electron beam on the screen of the cathode ray tube.

17. An apparatus for indicating, or for recording images of internal inhomogeneities in otherwise homogeneous bodies which have a substantially plane or slightly curved surface by ultrasonic examination according to the pulse echo method, comprising an ultrasonic apparatus having at least one angle probe connected thereto and indicating means responsive thereto which, by being activated when reflected sound pulses are received by said ultrasonic apparatus produce punctiform markings on a substantially plane recording surface, characterized by means to move the indicating means having an axis of indication along which the markings on the recording surface are made to thereby move this axis in the plane of the recording surface so that the displacement of a reference point on the axis of indication in relation to the recording surface follows the two-dimensional displacement of the sound emission point of the probe in relation to the surface of the body on a predetermined scale, the direction of the axis of indication in relation to the recording surface following the direction of the projection of the sound path on the surface of the body, the indicating means producing markings at a distance from the reference point that is proportional to the time interval that has elapsed from the emission to the reception of a sound pulse.

18. An apparatus as claimed in claim 17 further including a recording material placed immediately above and parallel to the surface of the examined body and rigidly connected thereto, the indicating means being in rigid connection with the probe so that the axis of indication is coincident with the projection of the sound path on the recording material, and that the reference point is coincident with the sound emission point.

19. An apparatus as claimed in claim 18, characterized in that a holder provided with at least one line of indicating units is mounted in rigid connection to the probe, which indicating units are mounted at fixed intervals along a straight line which coincides with the projection of the sound path on the plane of the recording material, and control circuits connecting each individual indicating unit to the receiver part of the ultrasonic apparatus so that the individual indicating unit is activated and produces a punctiform marking on the recording material when and only when a signal is generated from a reflected sound pulse, the distance from the sound emission point of the probe to the indicating unit being activated being proportional to the total time taken by said pulse for forward and return travel in the body.

20. An apparatus as claimed in claim 19, characterized in that the indicating units are electrically activated styluses responsive to each said signal to produce a punctiform marking on the associated recording material.

21. An apparatus as claimed in claim 17, characterized in that a holder provided with at least one line of light diodes is mounted in rigid connection to the probe, which light diodes are mounted at fixed intervals along a straight line which substantially coincides with the projection of the sound path on the surface of the body, and control circuits connecting each individual light diode to the receiver part of the ultrasonic apparatus so that the individual light diode is activated to appear as a luminous point when and only when a signal is generated from a reflected sound pulse, the distance from the sound emission point of the probe to the light diode being activated being proportional to the total time taken by said pulse for forward and return travel in the body.

22. An apparatus as claimed in claim 21 characterized in that the light diodes are adapted to produce punctiform markings wherein said recording material includes an associated photosensitive recording material placed immediately above and parallel to the surface of the examined body and rigidly connected thereto, the light diodes producing punctiform markings thereon.

23. An apparatus as claimed in claim 21 wherein said recording material includes a photosensitive recording material placed above and parallel to the surface of the examined body in a stationary photographic camera whose shutter is open, the light diodes producing punctiform markings thereon.

24. An apparatus as claimed in claim 20, characterized in that, above each stylus (16) and on the side of holder (15) that is facing away from the surface (3) of the body, a substantially punctiform light diode (17) is additionally mounted that is activated simultaneously with the stylus (16) in question and thereby provides a visual indication every time a marking (8) is produced on the recording material (9).

25. An apparatus as claimed in claim 18 including a cathode ray tube connected to the ultrasonic apparatus, the screen thereof displaying video signals developed from the reflected sound pulses received by said ultrasonic apparatus, said video signals comprising luminous points or dashes along a time deflection axis and at distances that are proportional to the total time taken by the sound pulses in forward and return travel in the body, characterized in that the indicating means comprise flexible light conductors having a substantially punctiform cross-section, whose first end is mounted in rigid connection with the probe and facing the recording material, and whose second end in a holder is mounted immediately in front of and facing the screen of the cathode ray tube at a distance along the time deflection axis of the screen that is proportional to the distance from the sound emission point of the probe to the first end of the light conductor.

26. An apparatus as claimed in claim 18 characterized in that a holder is mounted in rigid connection with the angle probe, the holder displaceably mounting at least one indicating unit so that said indicating unit is displaceable along a straight line which is parallel to the projection of the sound path on the recording material, a position transducer for indicating the indicating unit's position, and control circuits connecting the holder to the receiver part of the ultrasonic apparatus in such a way that the indicating unit is activated and produces a punctiform marking on the recording material when and only when a signal is generated from a reflected sound pulse, the total time taken by which for forward and return travel in the body is proportional in a predetermined relationship to the distance from the sound emission point of the probe to the point where the indicating unit happens to be when the sound pulse is received.

27. An apparatus as claimed in claim 26, characterized by two shafts mounted in said holder, two rollers rotatably mounted on said shafts, an endless belt running around the rollers, said at least one indicating unit being mounted on the belt.

28. An apparatus as claimed in claim 26, characterized in that said indicating unit comprises a facsimile registration device with a cylinder provided with a helical projection and rotating around a shaft that is in rigid connection with the probe and is mounted parallel to the recording material.

29. An apparatus as claimed in claim 17, characterized in that said indicating means includes a substantially plane recording material arranged in a first holder, and including means connecting said holder to the examined body in such a way that the holder follows the two-dimensional displacement of said body in the plane of the surface on a predetermined scale, at least one indicating unit mounted in a conventional marking position in relation to the recording material and secured in a second holder and means connecting said holder to the angle probe in such a way that the holder follows the two-dimensional displacement of said probe across the surface of the body on the same predetermined scale.

30. An apparatus as claimed in claim 17 further including a cathode ray tube and intensity modulation means for producing luminous points on the screen of the cathode ray tube, a holding device rigidly connected to the examined body and mounting the angle probe head, in such a way that the probe can be unimpededly turned and displaced in a two-dimensional displacement across the surface of the body, the holding device including position transducers, electronic control circuit connecting the position transducers to the cathode tube so that its electron beam sweep follows a rectilinear track on the screen which, on a predetermined scale reproduces the position of the probe in relation to the body and the direction of the projection of the sound path on the surface of the body, the intensity modulation circuits controlling the beam so that it produces a luminous point on the screen when the probe receives a reflected sound pulse and at a distance from the point on the screen corresponding to the position of probe, which distance, on the same predetermined scale, is proportional to the time interval that has elapsed from the emission to the reception of the sound pulse.

31. An apparatus as claimed in claim 17 including two rectilinear microphones mounted at right angles to each other immediately above the surface of the examined body and parallel with the body, and two substantially punctiform sound sources are mounted for the emission of spherical sound waves, one of them immediately above the sound emission point of the ultrasonic probe and the other at a distance herefrom immediately above the projection of the sound path on the surface on the body, coordinate registration circuits connecting the microphones and the sound sources to the cathode ray tube in such a way that the time intervals from the emission to the rejection of the spherical waves are converted into such control voltages that the electron beam sweep of the tube at all times follows a rectilinear track on the screen which, on a predetermined scale, reproduces the position of the probe in relation to the body and the direction of the projection of the sound path on the surface of the body, and intensity modulation circuit means connecting the ultrasonic apparatus to the cathode ray tube so that its electron beam produces a luminous point on the screen when the probe receives a reflected sound pulse and at a distance from the point on the screen corresponding to the position of the probe which distance, on the same predetermined scale, is proportional to the time interval that has elapsed from the emission to the reception of the sound pulse.

* * * * *